(12) United States Patent
Stefanov et al.

(10) Patent No.: US 10,300,218 B2
(45) Date of Patent: May 28, 2019

(54) SAFETY ASSEMBLY FOR A MEDICAL DELIVERY DEVICE

(71) Applicant: CAREBAY EUROPE LTD, Sliema (MT)

(72) Inventors: Slobodan Stefanov, Deerfield Beach, FL (US); Johnathan Weiss, Pompano Beach, FL (US)

(73) Assignee: SHL MEDICAL AG, Zug (CH)

( * ) Notice: Subject to any disclaimer, the term of this patent is extended or adjusted under 35 U.S.C. 154(b) by 303 days.

(21) Appl. No.: 15/465,958

(22) Filed: Mar. 22, 2017

(65) Prior Publication Data

US 2018/0272075 A1    Sep. 27, 2018

(51) Int. Cl.
*A61M 5/20* (2006.01)
*A61M 5/32* (2006.01)
*A61M 5/315* (2006.01)

(52) U.S. Cl.
CPC ............ *A61M 5/3245* (2013.01); *A61M 5/20* (2013.01); *A61M 5/2033* (2013.01); *A61M 5/3157* (2013.01); *A61M 5/31566* (2013.01); *A61M 5/321* (2013.01); *A61M 5/3202* (2013.01); *A61M 5/3204* (2013.01); *A61M 5/326* (2013.01); *A61M 5/3243* (2013.01); *A61M 2005/206* (2013.01); *A61M 2005/208* (2013.01); *A61M 2005/2013* (2013.01); *A61M 2005/2026* (2013.01); *A61M 2005/2073* (2013.01); *A61M 2205/583* (2013.01); *A61M 2205/584* (2013.01)

(58) Field of Classification Search
CPC .... A61M 5/20; A61M 5/2033; A61M 5/3243; A61M 5/2345; A61M 5/2357; A61M 5/326; A61M 2005/2006; A61M 2005/2013; A61M 2005/3247; A61M 2005/3267
See application file for complete search history.

(56) References Cited

U.S. PATENT DOCUMENTS

| 6,679,864 B2 * | 1/2004 | Gagnieux ............. A61M 5/326 604/110 |
| 8,414,533 B2 | 4/2013 | Alexandersson |
| 2010/0152659 A1 | 6/2010 | Streit et al. |

(Continued)

FOREIGN PATENT DOCUMENTS

WO  2009/114542       9/2009
WO  2010/146358 A2   12/2010

*Primary Examiner* — Laura A Bouchelle
(74) *Attorney, Agent, or Firm* — McDonnell Boehnen Hulbert & Berghoff LLP

(57) ABSTRACT

A safety assembly for a medicament delivery device is presented that prevents premature activation or firing of the device during shipping or handling. The disclosed safety assembly uses a tubular cover partially contained inside of the housing of the delivery device that is axially slidable relative to the housing from a first position to a second position and then to a third position, the tubular cover having a housing nib and a cap nib, where each of the cap nib and housing nib protrudes radially outward from an outer surface of the tubular cover and are located at a proximal end of the tubular cover. In the first position the housing nib and cap nib are located outside of the housing with the housing nib abutting the terminal proximal face of the housing to prevent axial movement of tubular cover relative the housing.

20 Claims, 7 Drawing Sheets

(56) References Cited

U.S. PATENT DOCUMENTS

| | | | |
|---|---|---|---|
| 2011/0270198 A1* | 11/2011 | Perot | A61M 5/326 604/198 |
| 2012/0226233 A1* | 9/2012 | Schraga | A61M 5/3205 604/111 |
| 2014/0207077 A1 | 7/2014 | Iwase et al. | |
| 2016/0008542 A1 | 1/2016 | Hirschel et al. | |
| 2017/0043093 A1* | 2/2017 | Wotton | A61K 9/0019 |

* cited by examiner

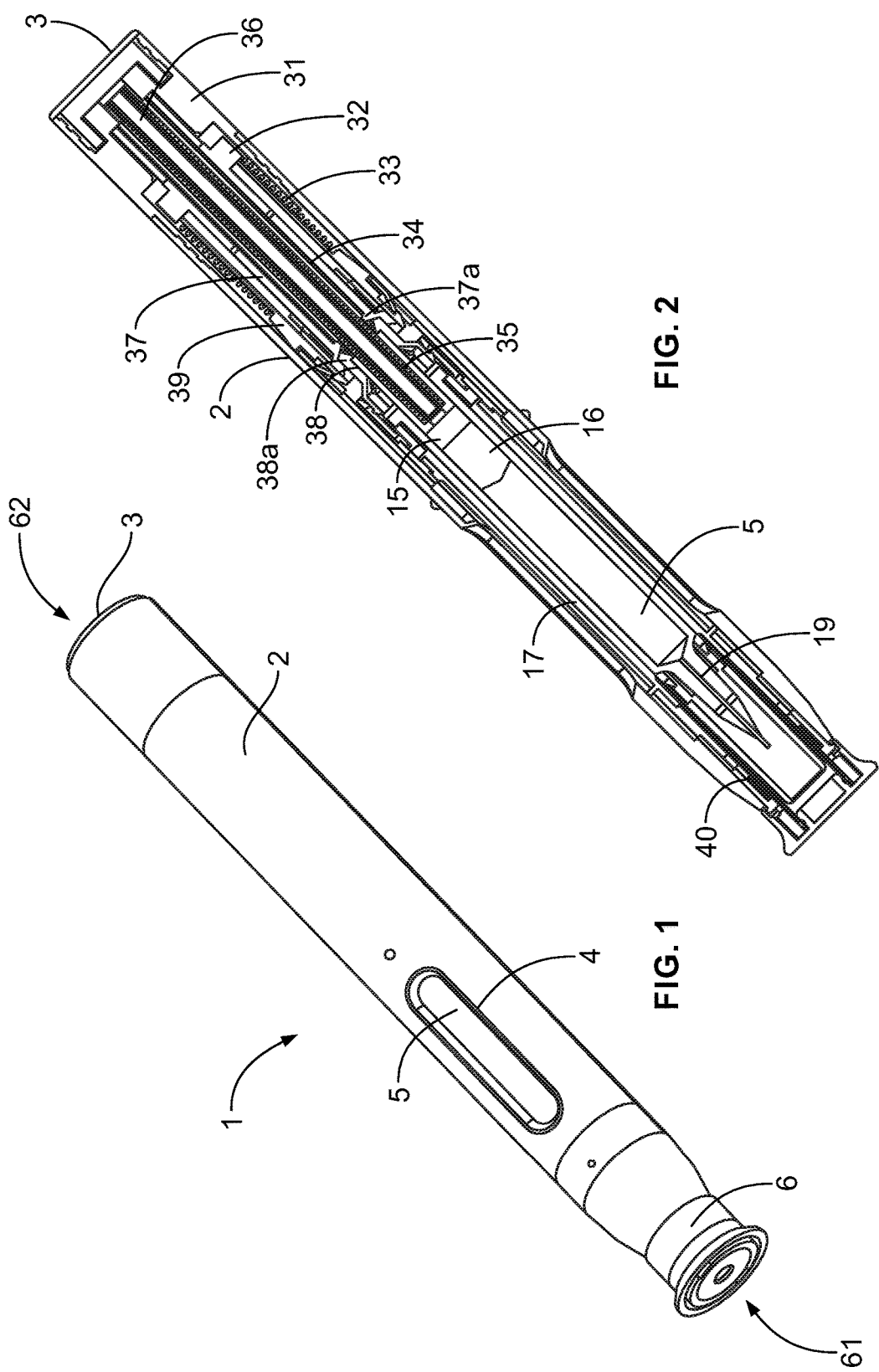

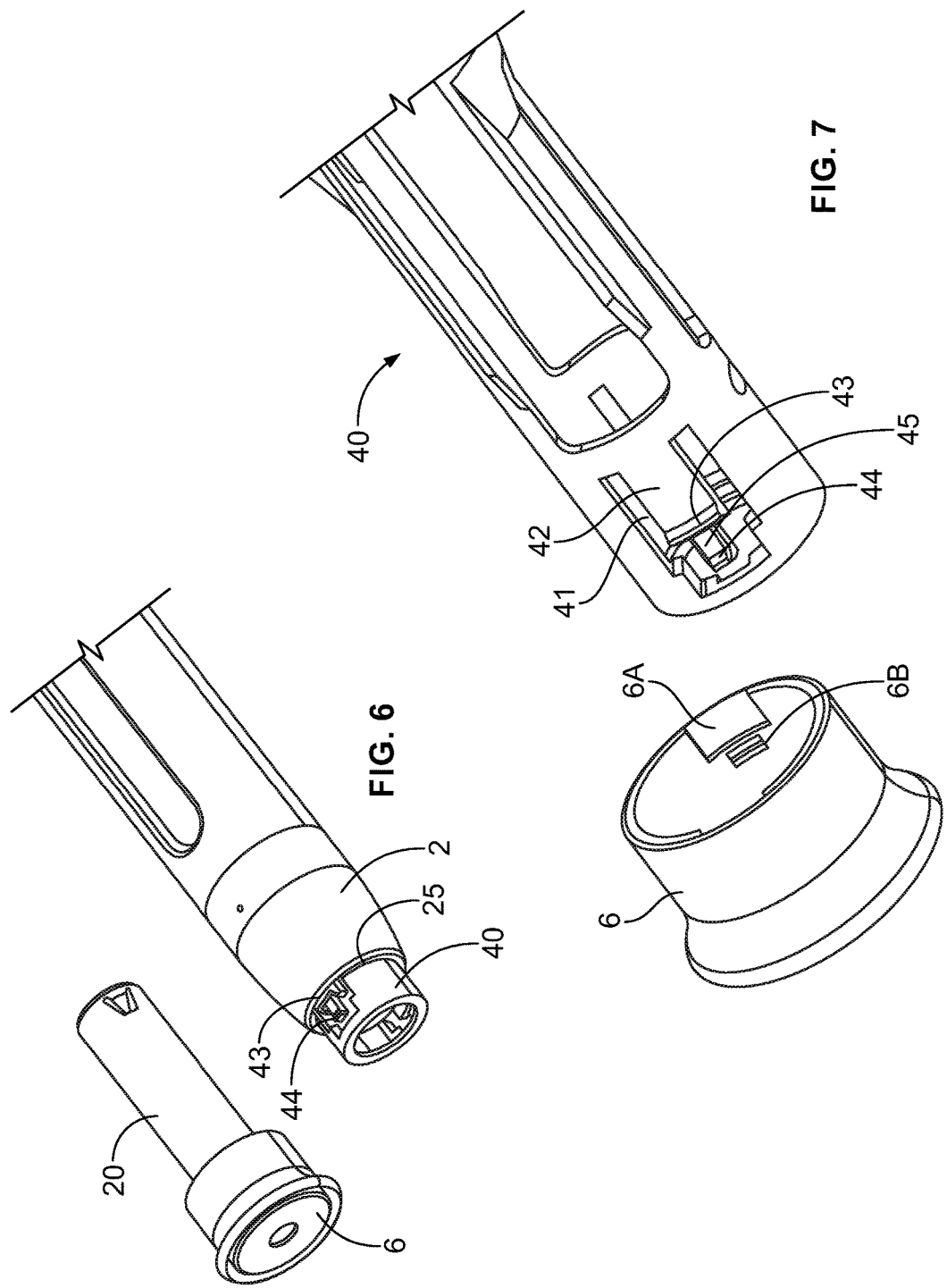

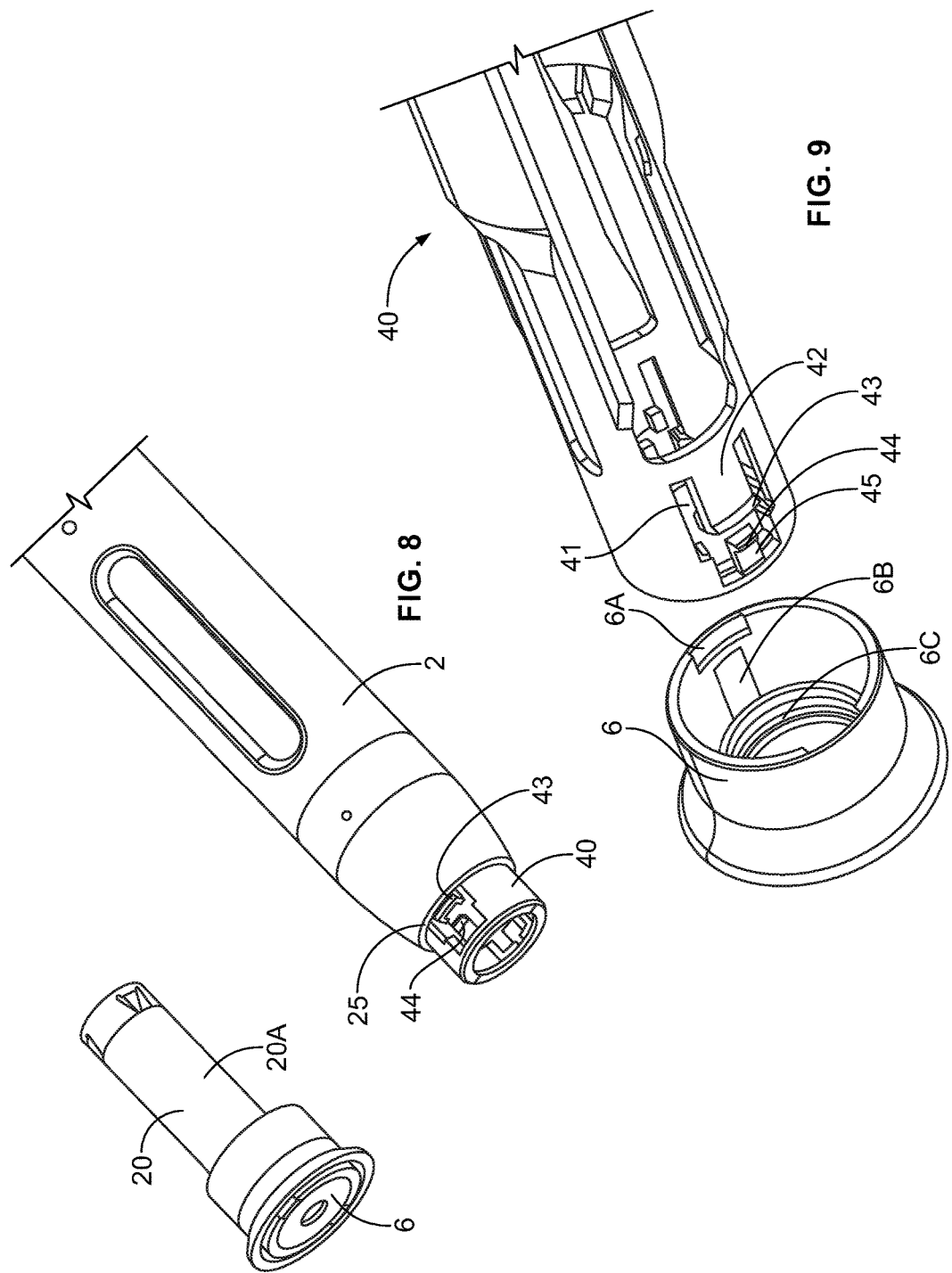

SAFETY ASSEMBLY FOR A MEDICAL DELIVERY DEVICE

TECHNICAL AREA

The present disclosure relates to a safety assembly for use with medicament delivery devices and in particular, to a protective needle shield component for use in a delivery device which provides for a secure connection of a cap assembly and that also prevents premature activation of the device prior to use.

BACKGROUND

There are a number of medicament delivery devices on the market that are capable of automatically or semi-automatically delivering doses of medicament. Such devices are constructed with a variety of inter-acting components for obtaining the desired functions, such as delivery of a medicament and after delivery lock out to prevent accidental needle sticks.

One type of such known delivery devices is an injector capable of delivering a fixed dose of medicament from a pre-filled syringe, having functions such as penetration of the patient's skin and a subsequent injection of medicament. One such particular device for example is disclosed in the U.S. Pat. No. 8,414,533, comprising an activation mechanism in the form of a button placed at its distal end. The button may only activate the mechanism if the front end of the device is pressed against an injection site. When the front end is pressed against the injection site and the button is pressed, the penetration mechanism inside the injector is released whereby the needle is pushed into the body of the patient. After this, the injection is performed. When the injection is completed, the patient withdraws the injector with the needle from the injection site, whereby a needle shield is pushed forward until it surrounds the needle and is then locked.

With an injector of the type described above, i.e., a so-called auto-injector, a pre-tensioned biasing element, typically a spring, is one of the components installed during manufacture and assembly of the device. This pre-tensioned or loaded biasing element provides the driving force to deliver the medicament when the user activates or fires the injector when placed on the injection site. Because of the pre-tensioned biasing member, there is a need to prevent, prior to the intended use of the injector, a premature firing or activation of the injector. In other words, during shipping and handling before the device is placed on the intended injection site it would be highly undesirable if the injector accidentally fired. Accordingly, manufacturers and distributors of these so-called auto-injectors have sought to develop and provide fail safe solutions or other safety solutions to prevent premature activation of the devices prior to the intended use.

Although some solutions to the above stated problems have been tried, there is still room for improvements. As presented in this disclosure, a new and improved tubular cover or needle shield is presented that solves the problem with a positive locking feature to prevent premature activation of a medical delivery device.

SUMMARY

Of course, the primary aim of the present disclosure is to remedy the drawbacks of known automatic injection devices, the so-called auto-injectors. Specifically, preventing the premature activation of the injectors before the user has placed the injector on the intended injection site.

One solution to the problem presented by this disclosure entails a safety assembly for a medicament delivery device that has a housing having a terminal face at a proximal end and a tubular cover partially contained inside of the housing and axially slidable relative to the housing from a first position to a second position and then to a third position, the tubular cover having a housing nib and a cap nib, where each of the cap nib and housing nib protrudes radially outward from an outer surface of the tubular cover and are located at a proximal end of the tubular cover, where in the first position the housing nib and cap nib are located outside of the housing with the housing nib abutting the terminal proximal face of the housing, where in the second position both the cap nib and housing nib are positioned inside of the housing, and where in the third position both the cap nib and the housing nib are located outside of the housing and the housing nib is not in abutment with the housing and the tubular cover is axially locked to prevent movement relative to the housing.

The safety assembly of the present disclosure also can contain a removable cap assembly that has a shield remover and having an inner surface comprising a releasable snap lock configured to operatively engage the cap nib when the tubular cover is in the first position. The shield remover can be configured to operatively lock the housing nib in the abutment with the terminal proximal face of the housing when the tubular cover is in the first position. Additionally, the releasable snap lock can have a radial bead projecting inwardly that engages and exerts a force on the cap nib during removal of the cap assembly from the safety assembly. The inner surface of the cap assembly has can have an indent configured to accept and cover the housing nib when the cap assembly is connected to the safety assembly.

With regard to the housing tab this can include an inner surface having a bearing surface projecting radially inward that operatively engages the shield remover to prevent inward radial movement of the housing tab when the cap assembly is connected to the safety assembly. The tubular cover when in the first and third positions protrudes from the proximal end to define a safety shield at a proximal end of the outer surface, the safety shield comprises a cut-out portion that defines a flexible finger comprising a cap tab operatively associated with the cap nib and a housing tab operatively associated with the housing nib, the cap tab and housing tab are positioned in a plane defined by the outer surface, and where each tab flexes radially inward out of the plane when a force applied to the nib associated with the tab. The cap nib can be located at a proximal end of the cap tab or the cap nib can be located at a distal end of the cap tab. In some cases, it is preferable that the cap nib and housing nib are aligned with each other along a longitudinal axis of the housing.

The present disclosure is also directed to a safety assembly for a medical device, specifically an auto-injector, having a container of medicament having a delivery member, such as a needle, and a removable cap assembly having a shield remover. The safety assembly has a housing and a tubular cover partially contained inside of the housing, the tubular cover protruding from the proximal end of the housing to define a safety shield. The safety shield has an outer surface with a cut-out portion that defines two juxtaposed flexible fingers, where each flexible finger contains a tab that is positioned in a plane defined by the outer surface and terminating in a nib, where each nib protrudes radially outward from the tab and where each tab is configured to flex radially inward out of the plane upon application of a force applied to the nib associated with the tab. One of the juxtaposed flexible fingers can be a housing finger having a housing nib and the other juxtaposed flexible finger can be a cap finger having a cap nib. The safety assembly can further include a removable cap assembly containing a shield remover and having an inner surface comprising a releasable snap lock configured to operatively engage the cap nib. The releasable snap lock can contain a radial bead projecting inwardly that engages and exerts a force on the cap nib during removal of the cap assembly from the safety assembly.

The inner surface of the cap assembly can have an indent configured to accept and cover the housing nib when the cap assembly is connected to the safety assembly. The housing flexible finger further also can have an inner surface having a bearing surface projecting radially inward that operatively engages the shield remover to prevent inward radial movement of the housing flexible finger when the cap assembly is connected to the safety assembly.

The safety shield in the device can have a second cut-out oriented 180 degrees from the cut-out, where the second cut-out defines two juxtaposed flexible fingers, where each flexible finger comprises a tab that is positioned in a plane parallel with the outer surface of the safety shield and terminating in a nib, where each nib protrudes radially outward from the outer surface of the safety shield and where each tab is configured to flex radially inward out of the plane upon application of a force applied to the nib associated with the tab. The safety shield can also move axially relative to the housing from a first position to a second position and then to a third position, where in the first position the housing nib and cap nib are located outside of the housing with the housing nib abutting a terminal proximal face of the housing, where in the second position both the cap nib and housing nib are positioned inside of the housing with the housing tab being flexed radially inward, and where in the third position both the cap nib and the housing nib are located outside of the housing and the housing nib is not in abutment with the housing and the safety shield is axially locked to prevent movement relative to the housing.

There are a number of advantages with each of the embodiments of the present disclosure. Primarily, the housing nib prevents the tubular cover or safety shield from moving prematurely proximally such that it activates the medical device. The housing nib is prevented from radial movement because an abutment of an inner surface that operatively engages the shield remover to prevent inward radial movement. This abutment locks the housing nib to the terminal face of the proximal end of the housing and acts as a hard stop preventing the safety shield from moving distally into the housing. Another advantage of the devices of the present disclosure is that the cap nib provides a secure attachment of the cap assembly to medical device so that the cap assembly will not prematurely come off or be dislodged prior to the intended use of the medical device.

These and other aspects of, and advantages with, the present disclosures will become apparent from the following detailed description of the present disclosure and from the accompanying drawings.

BRIEF DESCRIPTION OF THE FIGURES

In the following detailed description of the safety assembly, reference will be made to the accompanying drawings, of which FIG. 1 is a perspective illustration of one possible medicament delivery device containing the structural components of the present disclosure;

FIG. 2 shows a cross-sectional side view of a medicament delivery device illustrated in FIG. 1;

FIG. 6 is perspective view of the proximal end of the medicament delivery device of FIG. 1 where the cap assembly is removed;

FIG. 7 is perspective view of the proximal end of the tubular cover and the removed cap of the present disclosure medicament delivery device of FIG. 1;

FIG. 8 is perspective view of the proximal end of another embodiment of the medicament delivery device of FIG. 1 where another embodiment of the cap assembly is removed;

FIG. 9 is perspective view of the proximal end of another embodiment of the tubular cover and the removed cap of the present disclosure medicament delivery device of FIG. 8;

DETAILED DESCRIPTION

Figure 3:
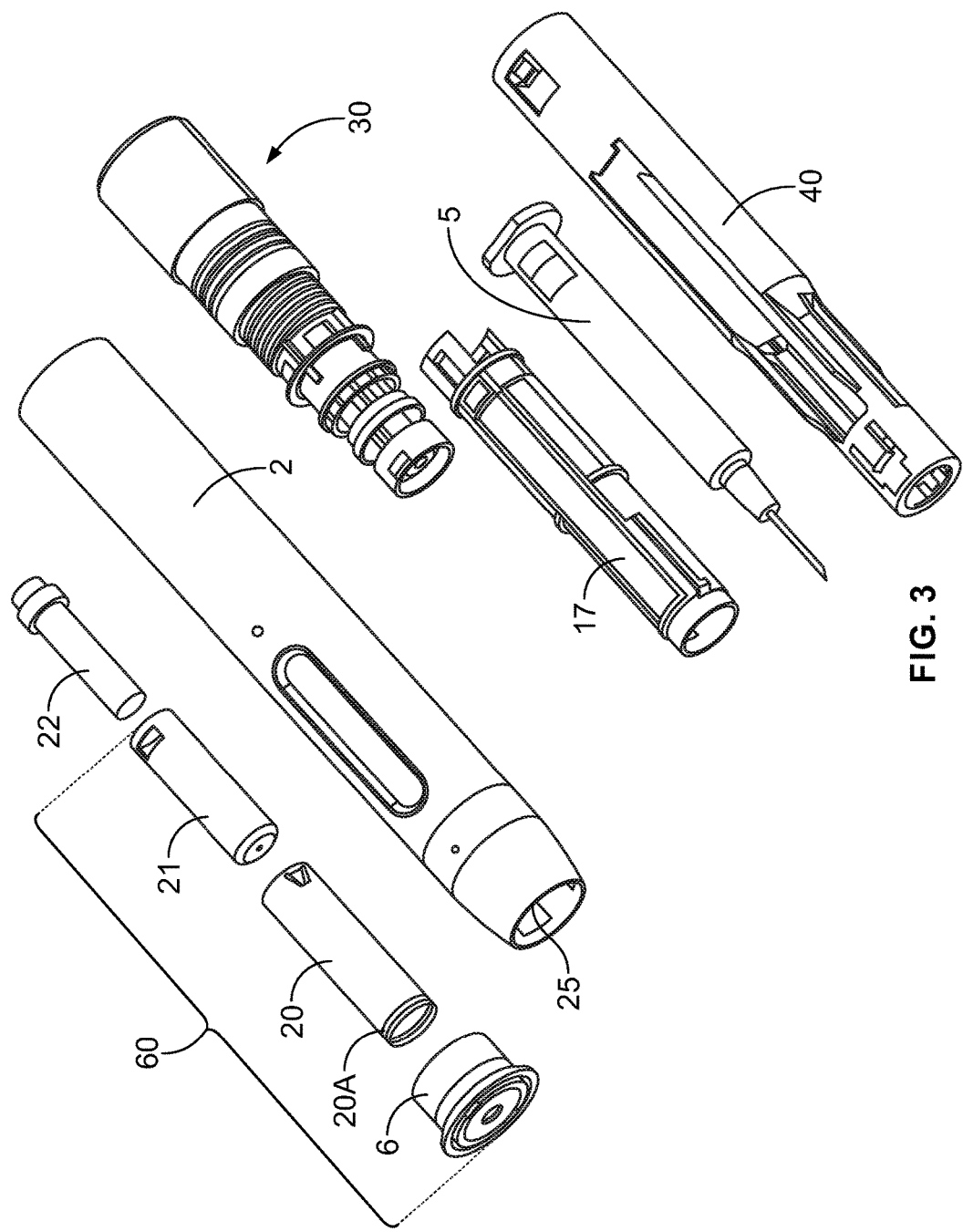
FIG. 3 is an exploded view of the medicament delivery device of FIG. 1.

In the present application, the term "distal part/end" refers to the part/end of the device, or the parts/ends of the members thereof, which in accordance with the use of the device, is located the furthest away from a delivery/injection site of a patient. Correspondingly, the term "proximal part/end" refers to the part/end of the device, or the parts/ends of the members thereof, which in accordance with the use of the device is located closest to the delivery/injection site of the patient.

The safety assembly of the present disclosure can be used in a number of injection devices to prevent premature activation of the devices. An example of such an injection device is the so-called auto-injector. One such embodiment of an auto-injector is illustrated in in FIG. 1, which is shown in a non-activated or pre-use condition as it would appear to a user after removal from its packaging. Injector 1 has a cap 6 as part of cap assembly 60 (see FIG. 3) and a generally elongated tubular housing 2 having opposite proximal 61 and distal 62 ends. The proximal end of housing 2 is arranged with an elongated opening 4 for viewing a barrel 5a of syringe 5 which contains a liquid medicament. Prior to activation of the device 1, only the medicament can be viewed inside the barrel of the syringe. In other words, plunger rod 34 (FIG. 5) cannot be seen through the opening 4. However, after the device is activated and the injection of medicament is complete, the plunger rod 34 can be seen through opening 4 as it is positioned inside barrel 5a (see FIGS. 12 & 13).

The device further comprises a tubular cover 40 (see FIGS. 2 and 3), hereinafter named needle shield, wherein the needle shield comprises a proximal part having a certain diameter and a distal part having a diameter larger than the proximal part, where these parts are joined by an intermediate conical part. The terminal proximal end face 46 is configured to allow the needle shield 40 to be placed at an injection site and is used as a bearing surface as the housing 2 is pushed proximally relative to the needle shield 40 to begin the injection activation sequence, as will be described in more detail below. Two elongated grooves are arranged along the needle shield 40, on opposite sides of the needle shield 40, also for viewing the syringe 5. At the distal end of the needle shield 40 two openings are arranged opposite each other, where each opening is arranged with a somewhat inwardly projecting, flexible, tongue. The needle shield sleeve 40 is slidably and coaxially arranged inside the housing 2 and the proximal part of the needle shield sleeve 40 protrudes a distance outside the proximal part of the housing 2.

The cap assembly 60 (see FIG. 3) includes a cap 6, a rigid shield remover (RSR) 20, and a Rigid Needle Shield (RNS) 21. Typically, the RSR 20 and RNS 21 are connected to the inside of cap 6 through a snap fit connection between bead 6c (see FIG. 9) with ring 20a (FIG. 3) on the proximal end of the RSR 20. The RSR 20 and the RNS 21 cooperate with each other to engage needle safety cover 22, which is part of the pre-filled syringe 5 assembly, and covers needle 19 (see FIG. 2) attached to the proximal end of syringe 5. When cap assembly 60 is placed on device 1 during the device assembly process the RNS 21 covers and engages needle safety cover 22 such that when the cap assembly 60 is ultimately removed from the device 1 prior to use, the safety needle cover 22 is gripped by the RNS 21 and RSR 20 so that the needle safety cover 22 is pulled off of syringe 5 when the cap assembly 60 is removed from the injector 1.

The proximal end of the needle shield 40 extends beyond the terminal end 25 of housing 2 (see FIGS. 6 and 8). Two possible embodiments of the needle shield 40 are presented in the present disclosure, with one configuration shown in FIGS. 6, 7, 10 and 12 and the other in FIGS. 8, 9, 11 and 13. In each configuration the proximal end of the needle shield 40 has a cut-out portion 41. Part of this cut-out portion 41 contains cover nib 44 and housing nib 43. The cover nib 44 is located at the end portion of flexible finger (cap finger) 45 and housing nib 43 is located at the end of another flexible finger (housing finger) 42. Each flexible finger comprises a tab that is positioned within the space defined by the cut-out portion 41, where the tab lies within a plane defined by the outer surface of the needle shield 40. Each tab terminates in one of the cover nib 44 and housing nib 43. In the embodiments presented herein, the housing nib 43 and cover nib 44 are axially aligned and part of single cut-out. Alternatively, the cover nib 44 and housing nib 43 could be radially offset from each other, i.e., not aligned axially, for example, the two nibs 43, 44 could be offset by 90 or 180 degrees, with each nib being part of a separate cut-out in the needle shield.

Figure 10:
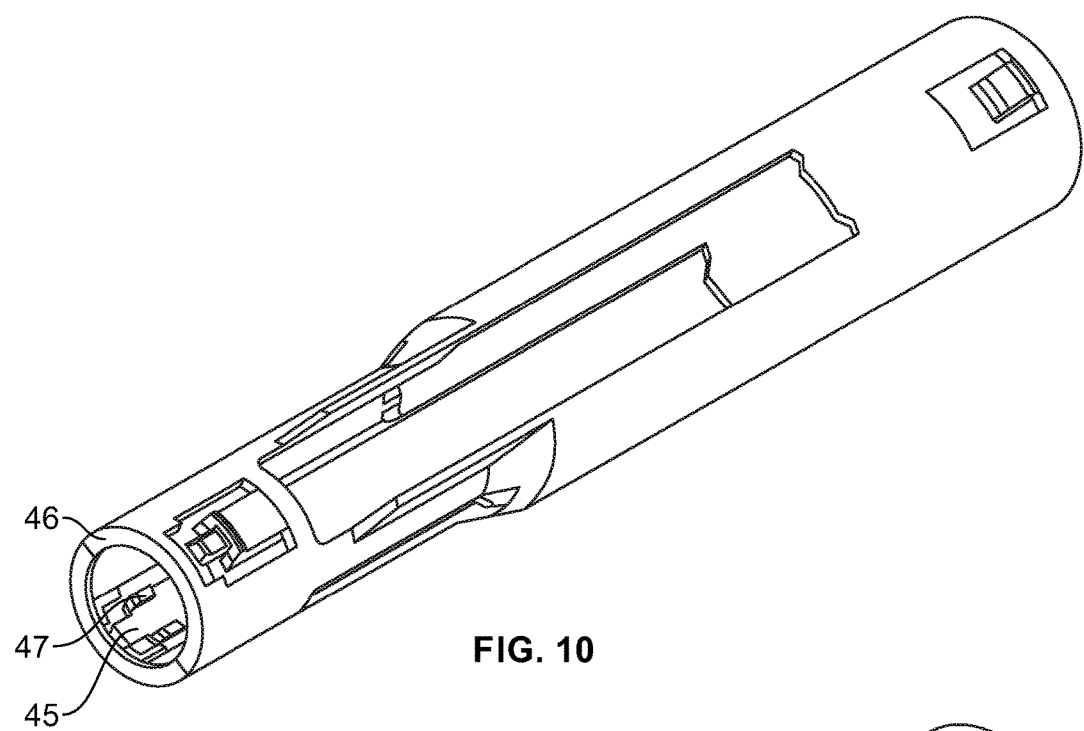
FIG. 10 is perspective view of the proximal end of the tubular cover of FIGS. 6 and 7.
Figure 11:
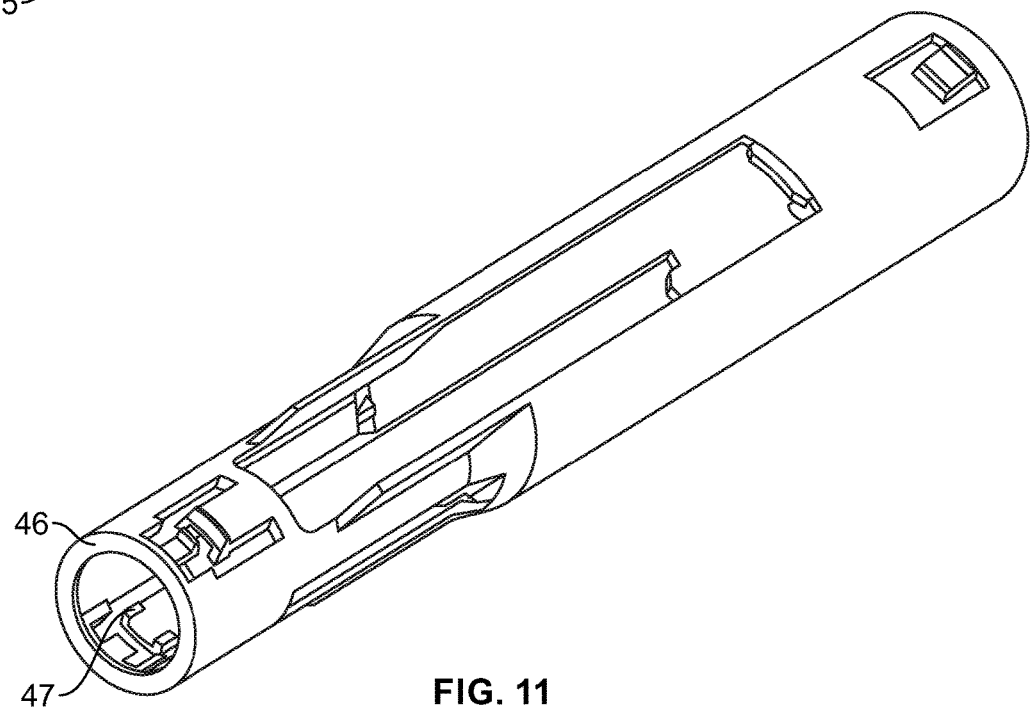
FIG. 11 is perspective view of the proximal end of the tubular cover of FIGS. 8 and 9.

In the embodiment illustrated in FIGS. 7 & 10, the cap finger 45 extends directly from the housing finger 42. In the alternative embodiment (FIGS. 9 & 11), the cap finger 45 extends from the proximal end of the cut-out portion 41 of the needle shield 40. In both embodiments, the housing finger 42 extends directly from the distal end of the cut-out portion 41.

FIGS. 6 & 8 show the position of the needle shield 40 immediately after the cap assembly 60 has been removed from the injector 1 and prior to placing the injector 1 at the injection site for delivery of the medicament in syringe 5. In both embodiments, when the cap assembly 60 is in place the outer surface of the RSR 20 prevents the housing finger 42 from flexing radially inward. This is achieved by the inward protrusion 47 (see FIGS. 10 & 11) that abuts the outer surface of RSR 20, thus preventing the housing finger 42 from bending inward radially. This keeps housing nib 43 firmly positioned against the terminal end face 25 of housing 2 and acts as a hard stop preventing any axial movement of the needle shield 40 in the distal direction. As such, when the device 1 is being shipped or otherwise handled with the cap assembly 60 connected to the injector 1, the needle shield 40 cannot prematurely move axially inside the housing 2 to cause an unwanted triggering or activation of the device 1. With the cap assembly 60 attached to the injector 1, the housing nib 43 is kept in direct abutment with the terminal end face 25 of housing 2.

Once the cap assembly 60 is removed from the injector, which in turn removes the RSR 20, then housing finger 42 is free to flex radially inward when the needle shield 40 is pushed against an injection site. The forceful axial movement of the needle shield 40 in the distal direction relative to the housing 2 causes housing nib 43 to deflect inwardly as the housing finger 42 bends inward, thus the housing nib 43 no longer acts as a hard stop as it moves out of abutment with the terminal end face 25.

For each of the two embodiments illustrated in FIGS. 6-11, the cap nib 44 functions as part of a releasable snap lock connection to keep the cap assembly 60 securely fixed to the injector 1. As indicated in the embodiment shown in FIGS. 6 & 7, the cap nib 44 is at the proximal end of cap finger 45. When the cap assembly 60 is connected to the injector 1 during device assembly, the cap 6 engages the cap nib 44 through snap connector 6b. A similar snap fit occurs in the other embodiment illustrated in FIGS. 8 & 9, where the cap nib 45 is located at the distal end of cap finger 45. In both cases the cap finger 45 and cap nib 44 flex inwardly when the cap 6 is pushed on the injector 1 and again when the cap 6 is pulled off the injector 1.

The device 1 also comprises a syringe carrier mechanism comprising a syringe carrier 17 slidably and coaxially arranged within the needle shield sleeve 40; the syringe 5 comprising a stopper 16, the medicament and a needle 19, wherein the syringe 5 is coaxially arranged within the syringe carrier 17; and a holding member connected to the syringe carrier 17. The syringe carrier 17 has the form of a general tubular body and the proximal part of the syringe carrier 17 is arranged with a neck portion of lesser diameter (see FIG. 3). Adjacent the neck portion cut-outs have been made on either side to form guide surfaces. These surfaces cooperate with corresponding shapes of the inner surface of the needle shield 40 in order to obtain a stop mechanism against rotation of the syringe carrier relative the needle shield. The distal end of the syringe carrier 17 is arranged with two distally extending tongues, where each tongue is arranged with an opening and an inwardly directed ledge on the distal edge of each opening. The syringe carrier 17 is further arranged with radial inwardly directed flanges on its inner surface in order to obtain a space between the syringe carrier wall and the syringe 5 to be placed inside.

Figure 4:
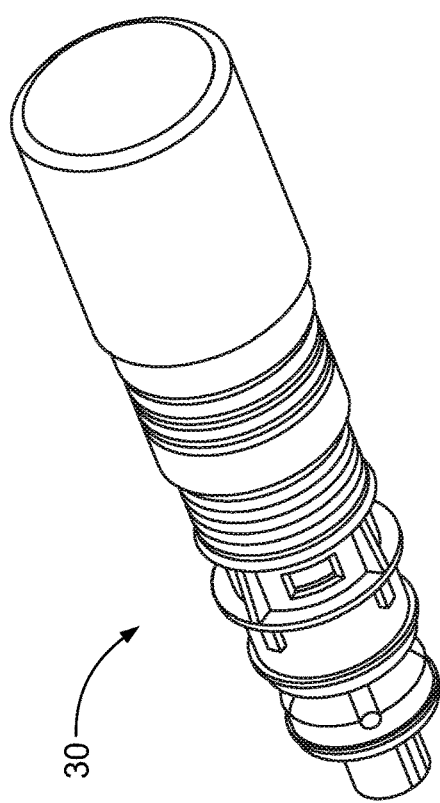
FIG. 4 is perspective view of a activator assembly of the medicament delivery device of FIG. 1.
Figure 5:
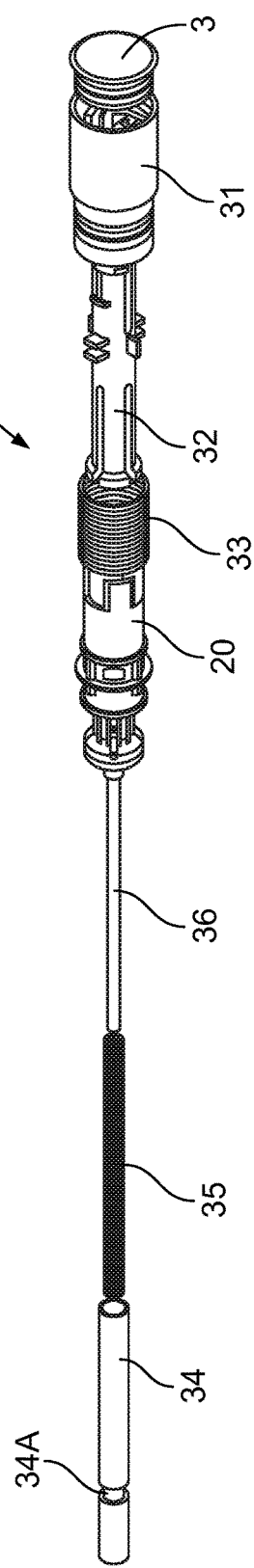
FIG. 5 is an exploded view of the activator assembly illustrated in FIG. 4.

The device 1 also comprises an activator assembly 30 that is generally shown in FIGS. 3, 4 & 5, with the exception of the rear cap 3 and the distal end of the housing 31 (see FIG. 5), which are not considered part of the activator assembly. The activator assembly is slidably and coaxially arranged within the housing 2 and connected to the needle shield sleeve 40 as will be described below. The activator assembly 30 also comprises a drive mechanism that is adapted to accumulate a drive force for moving the syringe carrier mechanism 17 in a first and a second step and, after completely expelling the medicament, to force the activator assembly 30 components towards the distal part of the elongated tubular housing for producing audible, visual and/or tactile feedback to a user about a completed injection. The cap 6 also has an indented portion 6a on the inside surface of the cap 6 that allows the cap 6 to pass over the housing nib 43 during cap placement and removal. This is necessary because, as explained above, housing finger 42 is prevented from flexing inwardly when the protrusions 47 are abutting the RSR 20, therefore the indented portion 6a provides the necessary clearance for the housing nib 43.

The drive mechanism comprises a plunger rod 34 arranged to act on the stopper 16 inside the syringe 5, and a first compression spring 35 that is pre-tensioned to have an accumulated force capable of urging the plunger rod 34 to move the syringe carrier mechanism in a first step for penetrating the needle 19 into an injection site and to move the stopper 16 in a second step for expelling the medicament through the needle. The plunger rod 34 is slidably and coaxially arranged within the activator mechanism 30 and the pre-tensioned first compression spring 35 is coaxially arranged within the plunger rod 34 between a proximal end wall of the plunger rod 34 and the distal transversal end wall of the drive mechanism. Further, a guide rod 36 is arranged inside the first compression spring 35 (see FIG. 5).

The plunger rod 34 is formed as a tube with an outer diameter somewhat smaller than the inner diameter of the syringe body to be used. The plunger rod 34 is arranged with a circumferential groove 34a to engage the ledges 37a of a second activator member 37 and the ledges 38a of a holding member 38 so that the annular inwardly directed ledges of the activator member 37 and the radial inwardly directed ledges of the holding member 38 fit into the circumferential groove of the plunger rod 34. The device further comprises a pre-tensioned second compression spring 33 having an annular proximal end resting on a second annular ring of the drive mechanism and an annular distal end resting on the proximal surface of stop ledges of the activator member.

The function of the device according to this disclosure will now be described. When the device 1 is assembled, the distal housing part is fixedly attached to proximal housing part by suitable engagement means forming the elongated tubular housing 2 and the first and the second activator members are coaxially movable relative each other. However, when the device 1 is in a non-activation position, the plunger 34 is held against the accumulated force of the pre-tensioned first compression spring 35 by the inwardly directed ledges 37a of the tongues of the second activator member 37 situated in the groove 34a of the plunger 34, and by the first activator member 39 which surrounds and prevents the inwardly directed ledges 37a of the tongues from moving radially outwards. Further, the ledges 38a of the holding member 38 are also arranged in the groove 34a (see FIG. 2). The inwardly directed ledges on the distal edge of each opening of the syringe carrier 17 pass the distal end surface of the annular ledge of the holding member for connecting the syringe carrier 17 to the holding member, and at the same time the tongues of the needle shield 40 fit the distal surface of the ledge of the first activator member 39 for connecting the needle shield 40 to the first activator member 39.

The needle shield sleeve 40 and the first activator member 39 connected to it are arranged to be moved coaxially and distally in relation to the housing 2 and to the second activator 37 member against the force of the pre-tensioned second compression spring 33, when the terminal end face 46 of the proximal part of needle shield sleeve 40 is pressed against the injection site. When the first activator member 39 moves distally as a result of the distal axial movement of the needle shield 40, the band-shaped part of the second activator 37 comes out from the surrounding of the first activator member 39 and the resilient properties of the inwardly directed ledges 37a of the tongues of the activator allows the proximal end of the tongues to flex radially outwards, causing the ledges to be released from the groove 34a of the plunger rod 34. However, the ledges 38a of the holding member 38 are still in the groove 34a of the plunger rod and with the proximal end surface against the distal end of the syringe carrier 17, whereby the accumulated force from the pre-tensioned first compression spring 35 urges the plunger rod to move in the first step, whereby a penetration of the needle into the injection site is performed.

When the syringe carrier 17, carrying with it syringe 5, has reached its most proximal position it is forced to a stop. However, the accumulated force of the pre-tensioned first compression spring 35 acting on the plunger rod 34 is so high that the ledges 38a of the holding member 38 are forced out of the groove 34a of the plunger rod 34.

The accumulated force from the pre-tensioned first compression spring 35 continues to urge the plunger rod 34 to move in the second step causing stopper 16 inside the syringe 5 to move and the liquid medicament to be injected into the patient until the stopper 16 reaches the inner proximal end of the syringe 5. After the liquid medicament has been injected and the distal end of the plunger rod 34 has passed the ledges of the second activator member 37, the inwardly directed ledges 37a of the tongues are radially moved inwards. Because the pre-tensioned first compression spring 35 is also acting on the inner surface of the distal transversal end wall of the second activator member 37 and has a remaining accumulated force, the second activator member 37 is moved distally until the outer surface of the distal transversal end wall of the second activator member 37 strikes against the inner surface of the distal wall of the distal housing part giving an audible signal to the patient indicating that the delivery e.g. the injection has been completed and that the device can be safely removed from the injection site.

Figure 12:
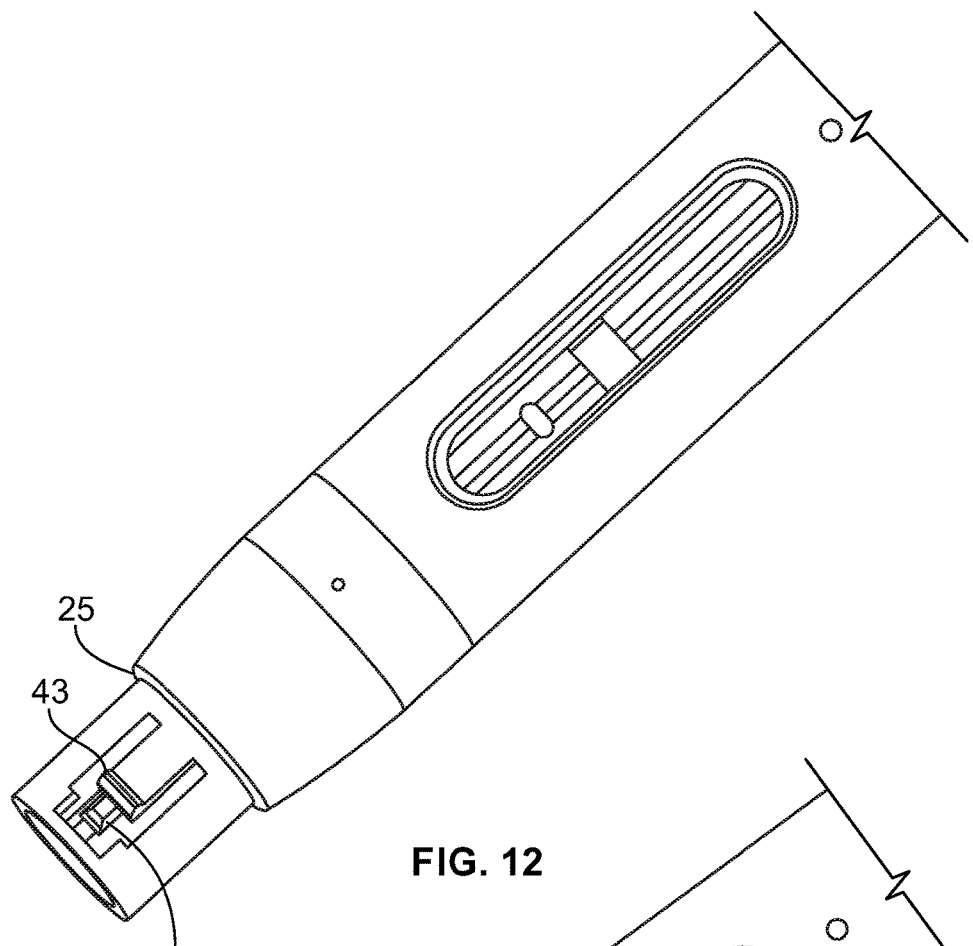
FIG. 12 is perspective view of the proximal end of the tubular cover of FIGS. 6 and 7 in the locked-out final position.
Figure 13:
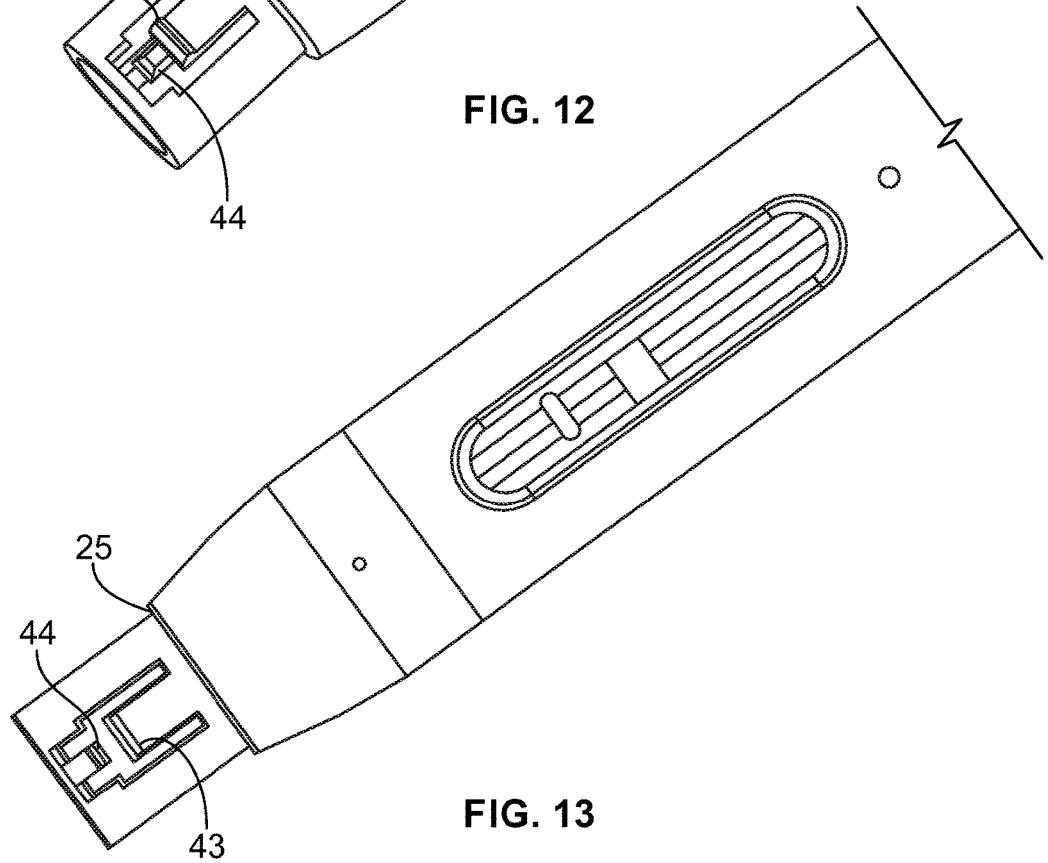
FIG. 13 is perspective view of the proximal end of the tubular cover of FIGS. 8 and 9 in the locked-out final position.

Further, as indicated in FIGS. 12 & 13, upon completion of injection, the plunger rod 34 can be viewed inside the syringe barrel 5a through opening 4 of housing 2 becoming tactile and/or visible to provide tactile and/or visual information indicating that the injection has been completed and that the device 1 can be safely removed from the injection site when the second activator member is coaxially and distally moved. In order to enhance the visibility, the plunger rod could be arranged with a bright color, differing from the color of the rest of the device.

The needle shield sleeve 40 and the first activator member are arranged to be coaxially and proximally moved in relation to the housing 2 and to the second activator member by a force from the pre-tensioned second compression spring 33 acting on the first activator member and thus on the needle shield 40 connected to it for covering the needle 19, when the proximal part of the needle shield sleeve 40 is removed from the delivery site. The first position of the needle shield 40 is illustrated in FIGS. 6 & 8. The first activator member comprises ribs on its inner surface arranged to interact with a band-shaped part of the second activator member after the needle shield sleeve 40 and the first activator member are coaxially and proximally moved, for preventing any attempts to push the needle shield sleeve 40 distally into the device, which prevents unintentional needle sticks. FIGS. 12 and 13 illustrate the axial position of the needle shield 40 for the two possible embodiments of the needle shield at the end of injection and after removal from the injection site. In both cases, the needle shield 40 extends proximally beyond the terminal end face 25 of the housing 2 such that both the housing nib 43 and cap nib 44 do not abut or engage the housing 2 in any fashion. This is the third position of the needle shield 40, where the first position is illustrated in FIGS. 6 and 8. The second position of the needle shield 40 is where the terminal end face 46 is pressed against the injection site such that the end face 46 is generally flush with the terminal end face 25 of housing 2 and where the housing nib 43 and the cap nib 44 are positioned inside and covered by housing 2.

It is to be understood that the embodiments described above and shown in the drawings are to be regarded only as non-limiting examples of the possible designs of the safety assembly and such designs may be modified in many ways within the scope of the patent claims.

The invention claimed is:

1. A safety assembly for a medicament delivery device comprising:
   a housing having a terminal face at a proximal end; and
   a tubular cover partially contained inside of the housing and axially slidable relative to the housing from a first position to a second position and then to a third position, the tubular cover having a housing nib and a cap nib, where each of the cap nib and housing nib protrudes radially outward from an outer surface of the tubular cover and are located at a proximal end of the tubular cover,
   where in the first position the housing nib and cap nib are located outside of the housing with the housing nib abutting the terminal proximal face of the housing, where in the second position both the cap nib and housing nib are positioned inside of the housing, and where in the third position both the cap nib and the housing nib are located outside of the housing and the housing nib is not in abutment with the housing and the tubular cover is axially locked to prevent movement relative to the housing.

2. The safety assembly of claim 1 further comprising a removable cap assembly comprising a shield remover and having an inner surface comprising a releasable snap lock configured to operatively engage the cap nib when the tubular cover is in the first position.

3. The safety assembly of claim 2 wherein the shield remover is configured to operatively lock the housing nib in the abutment with the terminal proximal face of the housing when the tubular cover is in the first position.

4. The safety assembly of claim 2 where the releasable snap lock comprises a radial bead projecting inwardly that engages and exerts a force on the cap nib during removal of the cap assembly from the safety assembly.

5. The safety assembly of claim 2 where the inner surface of the cap assembly has an indent configured to accept and cover the housing nib when the cap assembly is connected to the safety assembly.

6. The safety assembly of claim 2 where the housing tab further comprises an inner surface having a bearing surface projecting radially inward that operatively engages the shield remover to prevent inward radial movement of the housing tab when the cap assembly is connected to the tubular cover.

7. The safety assembly of claim 1 where the tubular cover in the first and third positions protrudes from the proximal end to define a safety shield at a proximal end of the outer surface, the safety shield comprises a cut-out portion that defines a flexible finger comprising a cap tab operatively associated with the cap nib and a housing tab operatively associated with the housing nib, the cap tab and housing tab are positioned in a plane defined by the outer surface, and where each tab flexes radially inward out of the plane when a force applied to the nib associated with the tab.

8. The safety assembly of claim 7 where the cap nib is located at a proximal end of the cap tab.

9. The safety assembly of claim 7 where the cap nib is located at a distal end of the cap tab.

10. The safety assembly of claim 1 where the cap nib and housing nib are aligned with each other along a longitudinal axis of the housing.

11. A safety assembly for a medical device comprising:
   a housing having a proximal end; and
   a tubular cover partially contained inside of the housing, the tubular cover protruding from the proximal end to define a safety shield, where the safety shield comprises an outer surface with a cut-out portion that defines two juxtaposed flexible fingers, where each flexible finger comprises a tab that is positioned in a plane defined by the outer surface and terminating in a nib, where each nib protrudes radially outward from the tab and where each tab is configured to flex radially inward out of the plane upon application of a force applied to the nib associated with the tab.

12. The safety assembly of claim 11 where one of the juxtaposed flexible fingers is a housing finger having a housing nib and the other juxtaposed flexible finger is a cap finger having a cap nib.

13. The safety assembly of claim 12 further comprising a removable cap assembly comprising a shield remover and having an inner surface comprising a releasable snap lock configured to operatively engage the cap nib.

14. The safety assembly of claim 13 where the releasable snap lock comprises a radial bead projecting inwardly that engages and exerts a force on the cap nib during removal of the cap assembly from the safety assembly.

15. The safety assembly of claim 13 where the inner surface of the cap assembly has an indent configured to accept and cover the housing nib when the cap assembly is connected to the the tubular cover.

16. The safety assembly of claim 13 where the housing finger further comprises an inner surface having a bearing surface projecting radially inward that operatively engages the shield remover to prevent inward radial movement of the housing flexible finger when the cap assembly is connected to the safety assembly.

17. The safety assembly of claim 11 where the safety shield further comprises a second cut-out oriented 180 degrees from the cut-out, where the second cut-out defines two juxtaposed flexible fingers, where each flexible finger comprises a tab that is positioned in a plane parallel with the outer surface of the safety shield and terminating in a nib, where each nib protrudes radially outward from the outer surface of the safety shield and where each tab is configured to flex radially inward out of the plane upon application of a force applied to the nib associated with the tab.

18. The safety assembly of claim 12 where the safety shield moves axially relative to the housing from a first position to a second position and then to a third position, where in the first position the housing nib and cap nib are located outside of the housing with the housing nib abutting a terminal proximal face of the housing, where in the second position both the cap nib and housing nib are positioned inside of the housing with the housing tab being flexed radially inward, and where in the third position both the cap nib and the housing nib are located outside of the housing and the housing nib is not in abutment with the housing and the safety shield is axially locked to prevent movement relative to the housing.

19. An injection device comprising:
   the safety assembly of claim 1;
   a container of medicament having a delivery member; and
   a removable cap assembly comprising a shield remover and having an inner surface comprising a releasable snap lock configured to operatively engage one of the nibs.

20. The injection device of claim 19 where the device comprises an auto-injector.

* * * * *